(12) United States Patent
Niu et al.

(10) Patent No.: US 9,784,649 B2
(45) Date of Patent: Oct. 10, 2017

(54) SILTY FLOATING MUD COLLECTION DEVICE

(71) Applicant: CCC THIRD HARBOR CONSULTANTS CO., LTD., Shanghai (CN)

(72) Inventors: Jianding Niu, Shanghai (CN); Jianping Hu, Shanghai (CN); Zhiyong Chen, Shanghai (CN); Zekun Cheng, Shanghai (CN); Limin Cheng, Shanghai (CN); Xiaojie Li, Shanghai (CN); Jiaoshe Dong, Shanghai (CN); Nianxi Wang, Shanghai (CN); Zhaoming Wang, Shanghai (CN)

(73) Assignee: CCC THIRD HARBOR CONSULTANTS CO., LTD., Shanghai (CN)

( * ) Notice: Subject to any disclaimer, the term of this patent is extended or adjusted under 35 U.S.C. 154(b) by 79 days.

(21) Appl. No.: 14/904,689

(22) PCT Filed: Nov. 14, 2013

(86) PCT No.: PCT/CN2013/087104
§ 371 (c)(1),
(2) Date: Jan. 12, 2016

(87) PCT Pub. No.: WO2015/007035
PCT Pub. Date: Jan. 22, 2015

(65) Prior Publication Data
US 2016/0153869 A1  Jun. 2, 2016

(30) Foreign Application Priority Data

Jul. 18, 2013 (CN) .......................... 2013 1 0304584
Jul. 18, 2013 (CN) .......................... 2013 2 0430416

(51) Int. Cl.
*G01N 1/10* (2006.01)
*E21B 25/10* (2006.01)
(Continued)

(52) U.S. Cl.
CPC ............... *G01N 1/10* (2013.01); *E21B 25/10* (2013.01); *E21B 25/14* (2013.01); *E21B 49/025* (2013.01);
(Continued)

(58) Field of Classification Search
CPC ............... G01N 2001/085; G01N 1/08; G01N 2001/1025; G01N 1/10; E21B 25/10;
(Continued)

(56) References Cited

U.S. PATENT DOCUMENTS 1,896,106 A * 2/1933 Simmons .................. E21B 4/14
173/206
3,409,094 A * 11/1968 Kretschmer ............ E21B 21/10
175/242
(Continued)

FOREIGN PATENT DOCUMENTS

CN 202033212 U 11/2011
CN 102818715 A 12/2012
(Continued)

*Primary Examiner* — Justin Olamit
(74) *Attorney, Agent, or Firm* — Global IP Services; Tianhua Gu

(57) ABSTRACT

A silty floating mud collection device, which includes a drive cylinder, an outer sleeve, a sampler barrel, an lug cover plate, a turning cover, a control ring and a control rod, where the drive cylinder includes a cylinder liner, a piston and a piston rod; the outer sleeve is fixedly connected below the cylinder liner; the sampler barrel is detachably installed inside the outer sleeve; the lug cover plate is fixedly connected to a lower end of the piston rod, and can close an upper-end opening of the sampler barrel; the turning cover (Continued)

is turnably installed at a lower end of the outer sleeve, and can close a lower-end opening of the sampler barrel; the control ring is located below the sampler barrel, and is used to block the turning cover which is in an open state; and an upper end of the control rod is connected to the lug cover plate, and a lower end of the control rod is connected to the control ring.

10 Claims, 6 Drawing Sheets

(51) Int. Cl.
    *E21B 49/02*     (2006.01)
    *E21B 25/14*     (2006.01)
    *G01N 1/08*     (2006.01)

(52) U.S. Cl.
    CPC .................. *G01N 2001/085* (2013.01); *G01N 2001/1025* (2013.01)

(58) Field of Classification Search
    CPC .......... E21B 25/14; E21B 25/18; E21B 49/02; E21B 49/025
    See application file for complete search history.

(56) References Cited

U.S. PATENT DOCUMENTS

| | | | | |
|---|---|---|---|---|
| 3,949,497 | A * | 4/1976 | Crump | ................. E02F 3/4131 175/253 |
| 6,695,078 | B2 * | 2/2004 | Kim | ........................ E21B 49/02 175/20 |
| 2011/0179888 | A1 | 7/2011 | Danesh | |

FOREIGN PATENT DOCUMENTS

| | | |
|---|---|---|
| CN | 202648989 U | 1/2013 |
| JP | 2004045081 A | 2/2004 |

\* cited by examiner

SILTY FLOATING MUD COLLECTION DEVICE

CROSS REFERENCE TO RELATED PATENT APPLICATION

The present application is the US national stage of PCT/CN2013/087104 filed on Nov. 14, 2013 which claims the priority of the Chinese patent applications No. 201310304584.7 filed on Jul. 18, 2013 and No. 201320430416.8 filed on Jul. 18, 2013, which applications are incorporated herein by reference.

BACKGROUND OF PRESENT INVENTION

Field of Invention

The present invention relates to a silty floating mud collection device of coastal engineering, and more specifically belongs to the field of sampling and testing technologies.

Description of Related Arts

Exploitation of nautical depth resources is: navigating by using a floating mud layer below a current water depth in a silty port area waterway and a coastal waterway having a silt property, which not only can increase a navigable depth, but also can reduce maintenance costs for the navigable depth, prolong a maintenance dredging period for ports, waterways and berths, and improve port economic benefits. Since the 80s of the 20th century, China began to develop and apply the nautical depth at some ports, and released a Ministry of Communications industry standard "Silty Seaport Nautical Depth Application Technology Specification" (JTJ/T325-2006), which is then enforced as a formal standard in China. To determine characteristics of a nautical floating mud layer thickness, it is needed to collect floating mud samples of different layers in an underwater back-silting layer, and to perform tests of particle composition analysis, sediment settling, density, silt rheological behavior, and the like. At present, a great progress has been made both in China and abroad in design and manufacture of a undisturbed soil sampler, and the representatives are: a fixed piston thin-wall soil sampler, single-rotary three (two)-barrel soil sampler, and the like, which all have relatively high soil sampling performance, and basically meet requirements of engineering geological survey. However, they are applied to stratum such as soft clay, sand gravel, and differentiated rock; because the floating mud layer involved in the nautical depth has an excessively high water content, so that the floating mud is in a flowing state. Obviously, the foregoing soil samplers cannot be applied to collect floating mud in a flowing state in different depths. In addition, the foregoing soil samplers use a direct pressing, hammer pressing or pressure rotating sampling manner, which cannot be applied to collect the floating mud either.

Because some sampling devices are of an opening manner, quality of samples will be affected by a lifting process, and deeper water indicates a larger impact.

For example, in China utility model patent 201020513399.0, a middle locking soil sampler is disclosed, which has a tubular structure and includes three parts: an upper soil sampling tube, a middle locking device, and a lower soil sampling tube. The upper soil sampling tube is connected to the middle locking device, the middle locking device is formed by a shaft valve seat and a shaft valve, the shaft valve is embedded in the shaft valve seat; the middle locking device is connected to the lower soil sampling tube; the upper soil sampling tube is a soil sampling inner tube, and an outer brake tube is installed at the outside of the upper soil sampling tube; a lower end portion of the outer brake tube has a vertical guide groove and an arc-shaped brake groove, the guide groove makes a suspension body move up and down only in a vertical direction, and the arc-shaped brake groove makes the shaft valve rotate only in a horizontal axial direction. Opening of the middle shaft valve depends on reaction of friction formed by soil and side wall of device, however reaction of a floating mud layer in a flowing state is very slight, which affects the opening, and therefore a sampling rate is reduced.

For another example, in China utility model patent 201220330329.0, a tooth-type sampler closing device is disclosed. The closing device includes a clasp guide rod, a retractable damping fin, a barrel body, and a tooth-type closing piece; the clasp guide rod is fixed at a lower end of a soil sampler, the clasp guide rod is mechanically connected to the barrel body in a sliding manner, an upper end of the barrel body is provided with the retractable damping fin, and a lower end of the barrel body is connected to the tooth-type closing piece by using a spring. When the soil sampler is drawn out, the damping fin is opened by using resistance of the mud, the barrel body moves down, and the closing piece closes the soil sample.

For still another example, in China utility model patent 201220330330.3, a backstop closed soil sampler is disclosed, which includes a piston, a soil sample tube, a backstop closing tube, and a movable shoe. The piston is sequentially connected to the soil sample tube, the backstop closing tube and the movable shoe; the piston, the soil sample tube and the backstop closing tube are fixedly connected together; the movable shoe is mechanically connected to the backstop closing tube in a sliding manner, and a backstop piece triggered by the movable shoe is installed inside the backstop closing tube. When the soil sampler is drawn out, the movable shoe will slide down by resistance of the mud, and then drive the backstop piece to close the soil sample.

Although all the foregoing three soil samplers may be applied to collecting underwater silty floating mud, but there are limitations. The first soil sampler is applicable to sampling when the surface of a river bed is in a soft plastic or plastic state. The second and the third soil samplers have the following problems: There are relatively large differences existing in water content, specific gravity, density, sand grain content of floating, flowing and silty mud, and soft or plastic soil, which form different friction; friction of floating and flowing mud is the smallest, and a high sampling rate cannot be achieved while a closing piece of the soil sampler is closed by control of friction. In addition, a lower-part structure of the first soil sampler uses vacuum negative pressure sampling, which is universally used in current survey technologies and is applicable to sampling of soft or plastic soil with a shape; the second and the third soil samplers use a closing device, which is an improvement for successively collecting floating mud, but the closing device is formed by backstop (closing) pieces, factors such as synchronous closing of the closing pieces and space between closing pieces all cause leaking of water in floating mud with high water content, and therefore affect accuracy of sample data.

Moreover, a sample upper opening cover during sample collecting is not considered in the prior art, and undisturbed state of the entire sample cannot be ensured.

SUMMARY OF THE PRESENT INVENTION

The technical problem to be solved in the present invention is to provide a silty floating mud collection device having a higher sampling quality, to overcome the foregoing defects of the prior art.

To resolve the foregoing technical problems, the present invention uses the following technical solutions: a silty floating mud collection device, comprising the following components: a drive cylinder, comprising a cylinder liner, a piston and a piston rod, wherein the piston fits to the inner wall of the cylinder liner in a sliding manner, and an upper end of the piston rod is fixedly connected to the piston; an outer sleeve, fixedly connected below the cylinder liner; a sampler barrel, detachably installed inside the outer sleeve, wherein upper and lower ends of the sampler barrel are both provided with an opening; an lug cover plate, fixedly connected to a lower end of the piston rod, and can close an upper-end opening of the sampler barrel; a turning cover, turnably installed at a lower end of the outer sleeve, and can close a lower-end opening of the sampler barrel; a control ring, located below the sampler barrel, and used to block the turning cover which is in an open state; and a control rod, wherein an upper end of the control rod is connected to the lug cover plate, and a lower end of the control rod is connected to the control ring.

Preferably, the silty floating mud collection device further comprises a drill coupling which is connected through thread to an upper end of the cylinder liner.

Preferably, a lower end of the cylinder liner is fixedly connected to a piston cover, and the piston cover is provided with a center hole for the piston rod to pass through.

Preferably, the piston cover is also provided with a vent hole.

Preferably, the outer sleeve is formed by connecting an intermediate cylinder, a two-halves tube and a turning rack, an upper end of the intermediate cylinder is connected to a lower end of the cylinder liner through thread; the two-halves tube is formed by combining two tubes, an upper end of the two-halves tube is connected to a lower end of the intermediate cylinder through thread, and a lower end of the two-halves tube is connected to the turning rack through thread; the turning cover is installed on the turning rack; and upper and lower ends of an outer wall of the sampler barrel are provided with a flange separately, and two ends of the two-halves tube is located between the flanges.

Further preferably, a side wall of the intermediate cylinder is opened with a through hole, and two ends of the lug cover plate reach out from the through hole and are connected to the control rod.

Further preferably, the turning cover is installed on the turning rack by using a hinge pin, and the hinge pin is sleeved with a torsional spring.

Preferably, there are two turning covers, which are symmetrically installed on a lower end of the outer sleeve in the left and right direction, and the two turning covers each are provided with a semicircular sealing gasket.

Further preferably, end portions of the two turning covers are lap-jointed to each other through an inclined plane.

Further preferably, two sides of the control ring are in contact with the two turning covers separately, and an upper edge of one side is higher than an upper edge of the other side.

Compared with the prior art, the present invention has the following beneficial effects:

(1) After the collection device reaches a specified depth, a drill rod applies pressure, so that the drive cylinder drives the lug cover plate and the turning cover to close the upper-end opening and the lower-end opening of the sampler barrel respectively, and therefore a mud sample can be kept in an undisturbed state well and is free from the influence of the environment, water depth, and the like, and a sampling rate is improved.

(2) Motive power of the drive cylinder can be provided by water pressure and air pressure formed in investigating the field, without needing to use another device.

(3) The entire collection device uses modular design and a standard structure, the costs are low, and disassembly is easy because parts are tightly connected through thread.

(4) The present invention can be used for sampling of floating mud at different depths of an underwater floating mud layer, and samples are kept in a natural, closed, and undisturbed state, and tests of particle composition analysis, sediment settling, density, silt rheological behavior, and the like are performed indoor according to the industry standard (JTJ/T325-2006), so as to provide a basis for determining a nautical depth of a waterway and harbor basin maintenance.

| | |
|---|---|
| 1. | Cylinder liner |
| 2. | Piston |
| 3. | Piston rod |
| 4. | Lug cover plate |
| 5. | Intermediate cylinder |
| 6. | Sampler barrel |
| 7. | Two-halves tube |
| 8. | Turning rack |
| 9. | Turning cover |
| 10. | Control rod |
| 11. | Control ring |
| 12. | Hinge pin |
| 13. | Piston cover |
| 14. | Seal ring |
| 15. | Drill coupling |
| 16. | Torsional spring |
| 20. | Outer sleeve |
| 41. | Lug |
| 51. | Through hole |
| 61. | Upper flange |
| 62. | Lower flange |
| 91. | Inclined plane |
| 7a. | Half tube |
| 7b. | Half tube |
| 9a. | Right turning cover |

-continued

| | |
|---|---|
| 9b. | Left turning cover |
| 111. | Control ring left side |
| 112. | Control ring right side |
| 131. | Vent hole |

DETAILED DESCRIPTION OF THE PREFERRED EMBODIMENTS

The present invention is further explained in detail with reference to the accompanying drawings and specific embodiments, and a person skilled in the art may understand other advantages and effects of the present invention more clearly.

It should be noted that, structures, ratios, and sizes drawn in the accompanying drawings of the specification are merely used to cooperate with the specific embodiments, to help a person skilled in the art to know conceptions of the present invention more clearly, but are not intended to limit the protection scope of the present invention. Any structure modification, ratio relationship change, or size adjustment without affecting implementation of effects and objectives of the present invention should fall within the protection scope of the present invention. For easy understanding, "upper", "lower", "left", and "right" in the following descriptions are all described according to a layout direction of the accompanying drawings of the specification.

Figure 1:
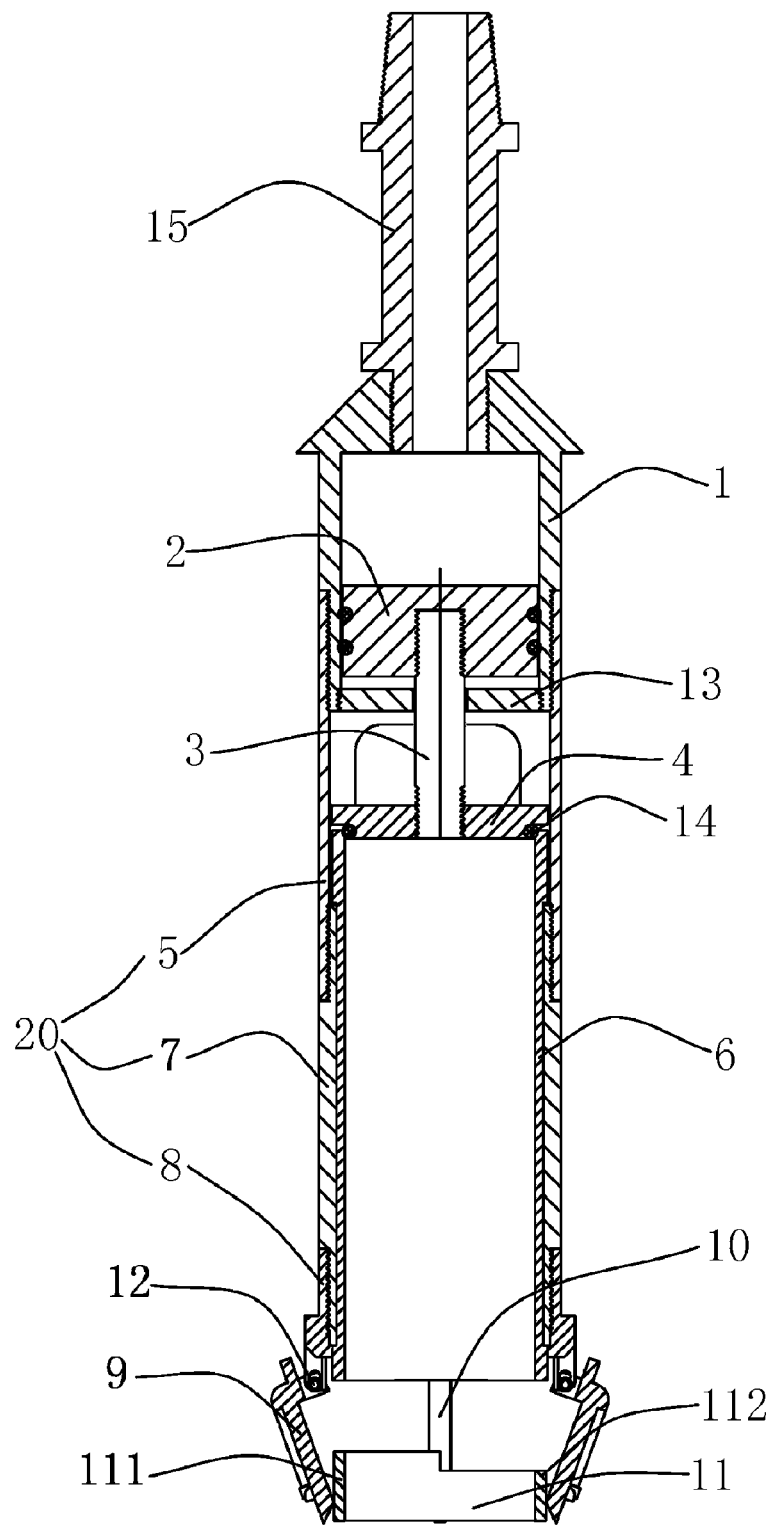
FIG. 1 is a schematic diagram of a sectional structure of a silty floating mud collection device consistent with the present invention.
Figure 2:
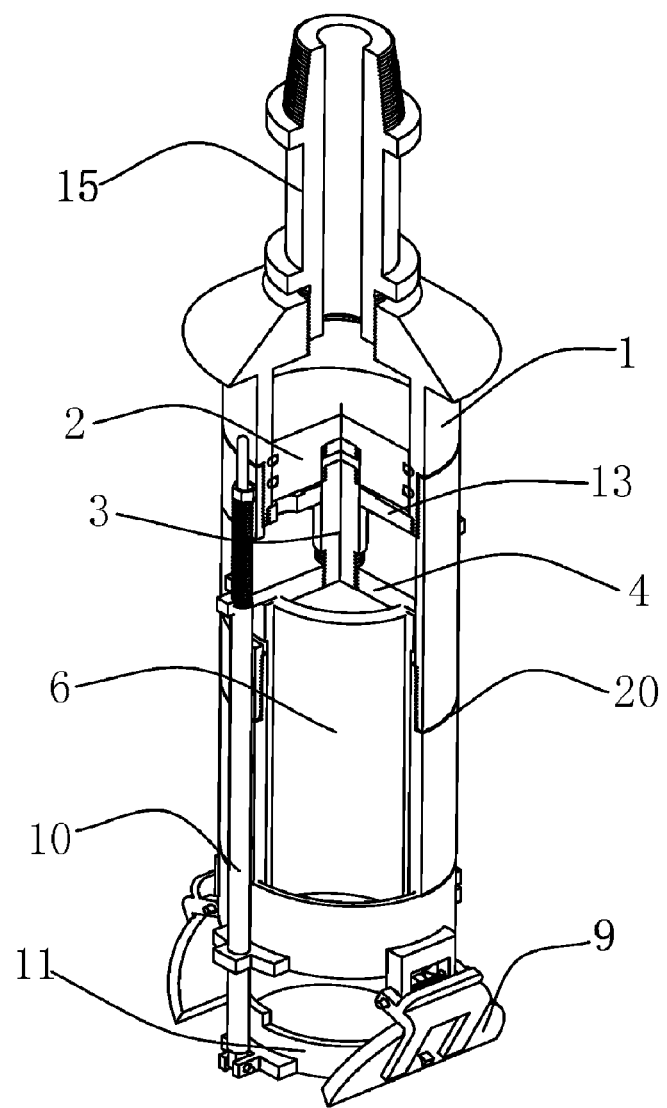
FIG. 2 is a three dimensional schematic diagram after partial sectioning of a silty floating mud collection device consistent with the present invention.

As shown in FIG. 1 and FIG. 2, a silty floating mud collection device consistent with the present invention comprises a drive cylinder, which comprises a cylinder liner 1, a piston 2 and a piston rod 3. A seal ring is disposed on a cylindrical surface of the piston 2, wherein the seal ring fits to an inner wall of cylinder liner 1 in a sealing manner, and can move up and down in an inner cavity of the cylinder liner 1. An upper end of the piston rod 3 is fixedly connected to the piston 2 through thread, and a lower end of the piston rod 3 extends into an outer sleeve 20 and is fixedly connected to a lug cover plate 4 through thread. A middle section of the piston rod 3 may be set to a square or hexagonal cross section, so as to screw thread by a wrench. The outer sleeve 20 is fixedly connected below the cylinder liner 1. A sampler barrel 6 is detachably installed inside the outer sleeve 20, and upper and lower ends of the sampler barrel 6 are both provided with an opening. An upper-end opening of the sampler barrel 6 is directly opposite to the lug cover plate 4, and can be closed by an undersurface of the lug cover plate 4. The undersurface of the lug cover plate 4 is provided with an O-shaped seal ring 14, which can fit to the upper-end opening of the sampler barrel 6 in a sealing manner. A lower end of the sampler barrel 6 exceeds a lower end of the outer sleeve 20, and a turnable turning cover 9 is installed at the lower end of the outer sleeve 20. In a preferable embodiment of the present invention, there are two turning covers 9, which are symmetrically installed on the lower end of the outer sleeve 20 in the left and right direction. When the turning cover 9 turns inward, a lower-end opening of the sampler barrel 6 can be closed, and a semicircular sealing gasket is disposed on each upper surface of the two turning covers 9, to ensure a sealing effect. A control ring 11, whose inner diameter is the same as that of the sampler barrel 6, is disposed below the sampler barrel 6 at a certain distance. When the turning cover 9 turns outward, a lower end of the turning cover 9 can be blocked by the control ring 11, and the turning cover 9 will keep staying in an open state. The control ring 11 is connected to a lower end of a control rod 10, and an upper end of the control rod 10 is connected to the lug cover plate 4. An upper end of the cylinder liner 1 is connected to a drill coupling 15 through thread. The drill coupling 15 is of a hollow, tubular structure, is in communication with the inner cavity of the cylinder liner 1, and can guide external air pressure or water pressure into the inner cavity of the cylinder liner 1, to drive the piston 2 to move up and down. An upper end of the drill coupling 15 is provided external thread, can connect through thread to a drill rod of a length, and the drill rod in a length direction extends vertically from a survey platform to the water surface, and then to a sampling point.

Figure 3:
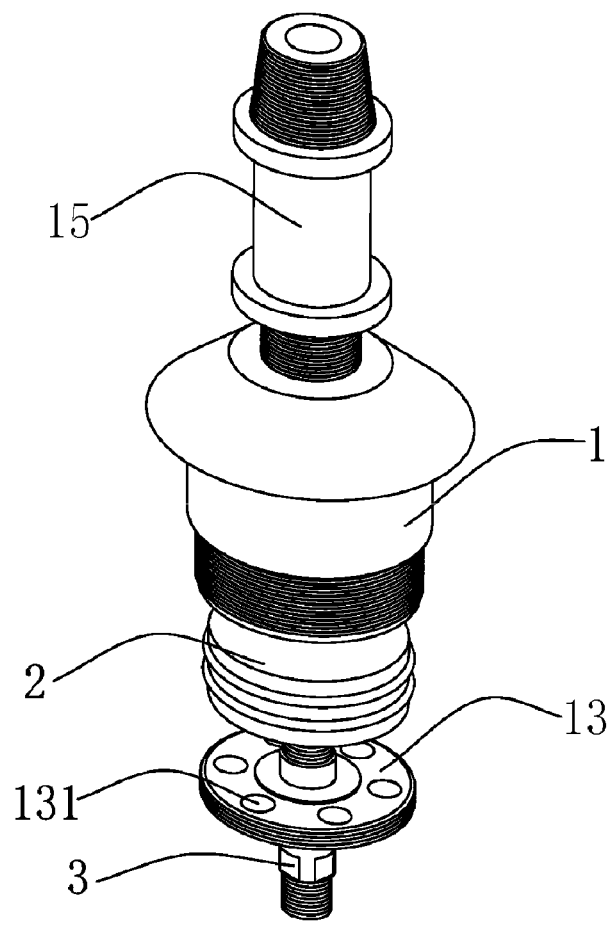
FIG. 3 is a schematic structural exploded view of an upper half of a silty floating mud collection device consistent with the present invention.

As shown in FIG. 1 and FIG. 3, to limit range of movement of the piston 2, a lower end of the cylinder liner 1 is fixedly connected to a piston cover 13. The piston cover 13 fits through thread to an inner wall of the cylinder liner 1, the piston cover 13 is provided with a center hole for the piston rod 3 to pass through, and the piston cover 13 is also provided with a vent hole 131. During a moving process of the piston 2, the vent hole 131 can have a function of balancing lower-part pressure of the piston 2.

Figure 7:
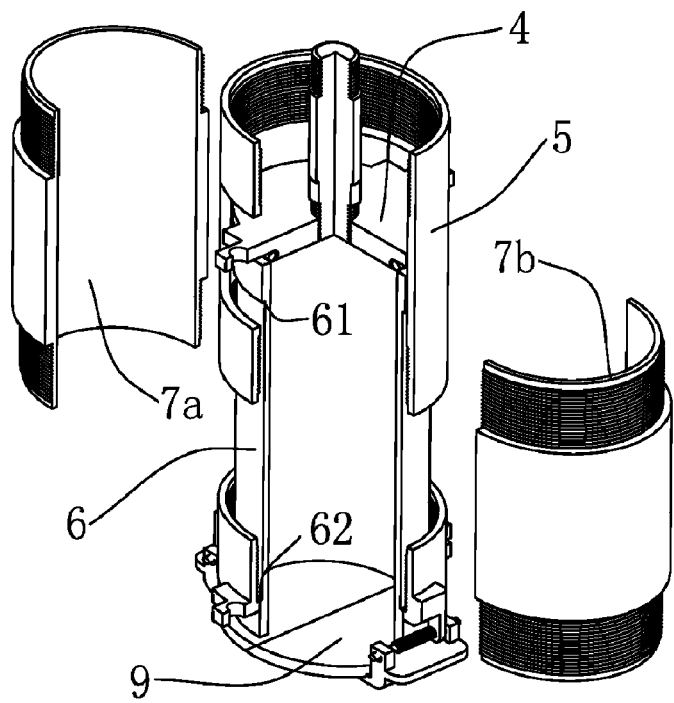
FIG. 7 is a schematic diagram of an installation manner of the sampler barrel according to the present invention.

Further, referring to FIG. 1 to FIG. 4, the outer sleeve 20 may be formed by connecting an intermediate cylinder 5, a two-halves tube 7 and a turning rack 8. An upper end of the intermediate cylinder 5 is connected to a lower end of the cylinder liner 1 through thread; the two-halves tube 7 is formed by combining two half tubes 7a and 7b (as shown in FIG. 7), an upper end of the two-halves tube 7 is connected through thread to a lower end of the intermediate cylinder 5, and a lower end of the two-halves tube 7 is connected through thread to the turning rack 8; the turning cover 9 is installed on the turning rack 8 by using a hinge pin 12, the hinge pin 12 is sleeved with a torsional spring 16, and the torsional spring 16 acts on a closed torque that is on the turning cover 9, that is, applies an action force on the turning cover 9 to make the turning cover 9 turn inward (close up). Certainly, the present invention does not exclude that the turning cover 9 may also turn under the action of other external forces.

Figure 4:
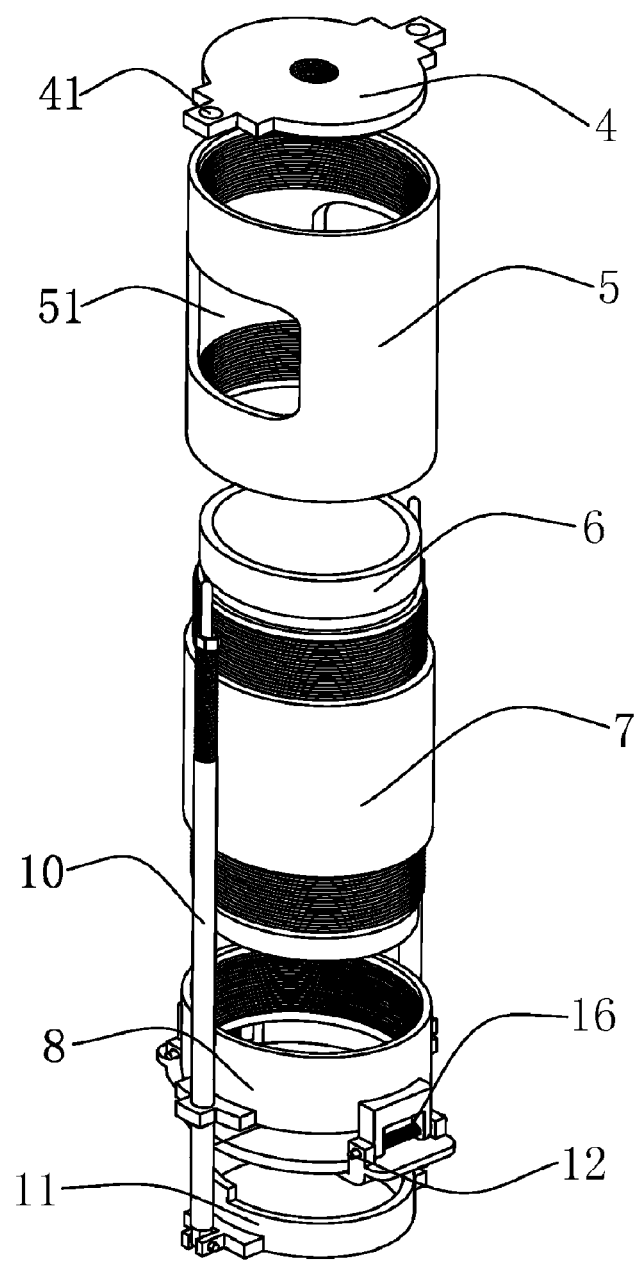
FIG. 4 is a schematic structural exploded view of a lower half of a silty floating mud collection device consistent with the present invention.

With reference to FIG. 4 and FIG. 7, upper and lower ends of an outer wall of the sampler barrel 6 are provided with flanges 61 and 62 respectively, and two ends of the two-halves tube 7 is located between the flanges 61 and 62, so as to axially limit the sampler barrel 6.

Figure 5:
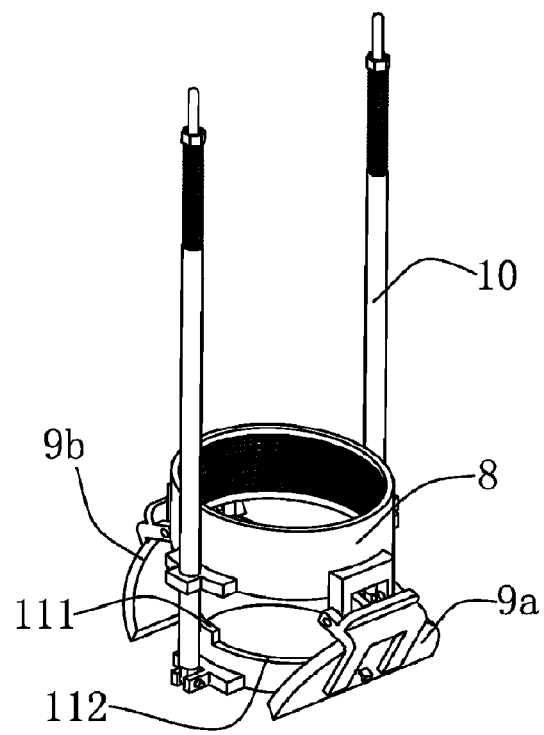
FIG. 5 is a schematic structural diagram of a turning cover which is in an open state according to the present invention.
Figure 6:
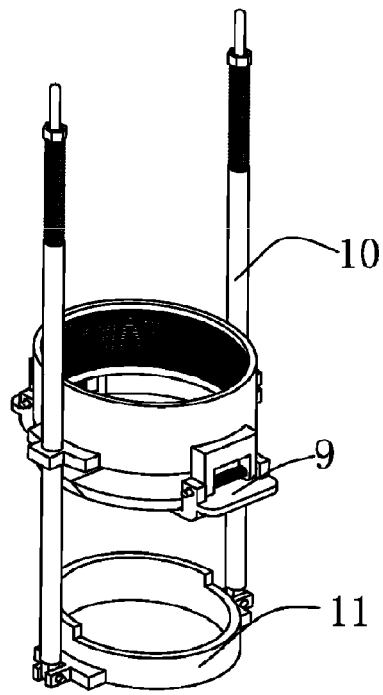
FIG. 6 is a schematic structural diagram of a turning cover which is in a closed state according to the present invention.

As shown in FIG. 4 to FIG. 6, a side wall of the intermediate cylinder 5 is opened with a rectangular through hole 51, the lug cover plate 4 may reach from through hole 51 into the inside of the intermediate cylinder 5, and lugs 41 at two ends of the lug cover plate 4 reach from the through hole 51 to the outside of the intermediate cylinder 5, and are connected to the control rod 10. When the lug cover plate 4 moves downward under the drive of the piston rod, the through hole 51 may also provide moving space for the lugs 41 at two ends of the lug cover plate 4. When the lug cover plate 4 moves downward, in one aspect, the upper-end opening of the sampler barrel 6 can be closed; in another aspect, the lug cover plate 4 drives the control ring 11 to move down by using the control rod 10, and when the control ring 11 is out of contact with the turning cover 9, the turning cover 9 turns inward and closes up under the action force of the torsional spring, and closes the lower-end opening of the sampler barrel 6.

Figure 8:
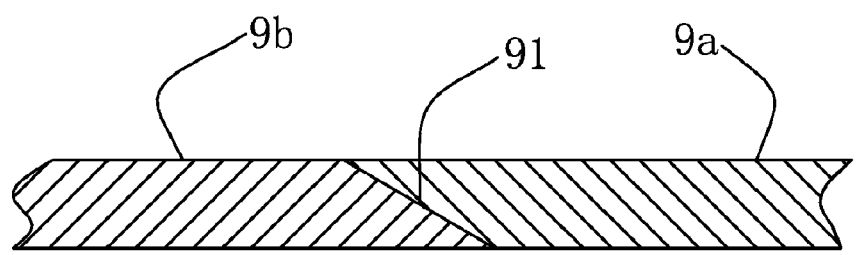
FIG. 8 is a schematic diagram of lap-jointing of two turning covers which are in a closed state according to the present invention.

As shown in FIG. 8, in a preferable embodiment of the present invention, end portions of two turning covers are both provided with an inclined plane 91; in a closed state, the end portions of the two turning cover 9a and 9b are lap-jointed through the inclined plane 91, which can increase a contact surface, and improve a sealing effect. But for this kind of lap joint, the two turning cover 9a and 9b need to be controlled to complete turning one after another, that is, the right turning cover 9a needs to turn up first, and then the left turning cover 9b turns up, so that inclined planes 91 of the two turning cover 9a and 9b overlap to form a lap joint. The present invention may achieve this effect by properly arranging a shape of the control ring. As shown in FIG. 5, an axial length of a control ring right side 112 in contact with the right turning cover 9a is relatively short, and a control ring left side 111 in contact with the left turning cover 9b is relatively long, that is, an upper edge of the control ring left side 111 is higher than an upper edge of the right side 112; in this way, when the control ring moves down under the drive of the control rod 10, the right turning cover 9a first comes out of contact with the control ring right side 112, and turns up first, and the left turning cover 9b then comes out of contact with the control ring left side 111, and turns up then, to form a lap joint.

A usage method of the present invention is described below.

As shown in FIG. 1 and FIG. 2, before sampling, the turning cover 9 is open, and a lower end of the turning cover 9 is supported on the control ring 11, so that the collection device is in a state for sampling. This device is connected under a drill rod, and inserted into underwater silt. When the soil is relatively hard, the control ring may have a guiding function. As the collection device goes down continuously, upper floating mud sequentially passes an inner wall of the control ring 11 and a lower-end opening and an upper-end opening of the sampler barrel 6, and is discharged from the through hole 51 until a specified depth. Then, air pressure of an air compressor or water pressure of a high pressure water pump is guided into the cylinder liner 1 through inner hole of the drill rod, to drive the piston 2 to move down, so that the lug cover plate 4 moves down to close the upper-end opening of the sampler barrel 6; meanwhile, the control ring 11 moves down along, the control ring 11 comes out of contact with the turning cover 9, and the turning cover 9 closes immediately under the action of the torsional spring, to close the lower-end opening of the sampler barrel 6. In this way, samples of the floating mud are sealed in the sampler barrel 6, then the drill rod is drawn up, and the sampler barrel 6 in the collection device is taken out on a survey platform. Steps are as follows: ① first make the control ring 11 face upwards, the drill coupling 15 face downwards, and the entire collection device be basically vertical to the survey platform; ② remove two nuts from the lower end of the control rod 10, take out the control ring 11 from the top, and screw off the turning rack 8; ③ screw on a sealing cover at the lower-end opening (which faces upwards currently) of the sampler barrel 6; ④ turn the collection device upside down then, make the sealing cover of the sampler barrel 6 face downwards, and the drill coupling 15 face upwards; ⑤ unscrew the piston rod 3, take out the lug cover plate 4; and unscrew the intermediate cylinder 5; ⑥ screw on a sealing cover at the upper-end opening of the sampler barrel 6, and then separate left and right two half tubes of the two-halves tube 7; ⑦ take out the sampler barrel 6, write identifiers such as a number and a soil penetration depth, paste it on the sampler barrel 6, circle a sealing strip at a gap between the sampler barrel 6 and the sealing cover and seal up by wax, store the sampler barrel 6 in a sample box, and carry it together to a laboratory to perform tests.

The present invention has a special design, a simple and practical structure, and is used for collecting samples of floating mud in an undisturbed state at different depths of an underwater floating mud layer, to perform tests of particle composition analysis, sediment settling, density, silt rheological behavior, and the like, so as to provide a basis for determining a nautical depth and harbor basin maintenance.

The above description of the detailed embodiments is only to illustrate the preferred implementation according to the present invention, and it is not to limit the scope of the present invention. Accordingly, all modifications and variations completed by those with ordinary skill in the art should fall within the scope of the present invention defined by the appended claims.

What is claimed is:

1. A silty floating mud collection device, comprising the following components:
   a drive cylinder, comprising a cylinder liner, a piston and a piston rod, wherein the piston fits to an inner wall of the cylinder liner in a sliding manner, and an upper end of the piston rod is fixedly connected to the piston;
   an outer sleeve, fixedly connected below the cylinder liner;
   a sampler barrel, detachably installed inside the outer sleeve, wherein upper and lower ends of the sampler barrel are both provided with an opening;
   a lug cover plate, fixedly connected to a lower end of the piston rod, and configured to close an upper-end opening of the sampler barrel;
   a turning cover, turnably installed at a lower end of the outer sleeve, and configured to close a lower-end opening of the sampler barrel;
   a control ring, located below the sampler barrel, and configured to block open the turning cover; and
   a control rod, wherein an upper end of the control rod is connected to the lug cover plate, and a lower end of the control rod is connected to the control ring.

2. The silty floating mud collection device as in claim 1, further comprising a drill coupling connected through thread to an upper end of the cylinder liner.

3. The silty floating mud collection device as in claim 1, wherein a lower end of the cylinder liner is fixedly connected to a piston cover, and the piston cover is provided with a center hole for the piston rod to pass through.

4. The silty floating mud collection device as in claim 3, wherein the piston cover is provided with a vent hole.

5. The silty floating mud collection device as in claim 1, wherein the outer sleeve is formed by connecting an intermediate cylinder, a two-halves tube and a turning rack, an upper end of the intermediate cylinder is connected through thread to a lower end of the cylinder liner; the two-halves tube is formed by combining two half tubes, an upper end of the two-halves tube is connected through thread to a lower end of the intermediate cylinder, and a lower end of the two-halves tube is connected through thread to the turning rack; the turning cover is installed on the turning rack; and upper and lower ends of an outer wall of the sampler barrel are each provided with a flange, and two ends of the two-halves tube are located between the flanges.

6. The silty floating mud collection device as in claim 5, wherein a side wall of the intermediate cylinder is opened with a through hole, and an end of the lug cover plate reaches out from the through hole and is connected to the control rod.

7. The silty floating mud collection device as in claim 5, wherein the turning cover is installed on the turning rack by using a hinge pin, and the hinge pin is sleeved with a torsional spring.

8. The silty floating mud collection device as in claim 1, wherein the turning cover is one of two turning covers symmetrically installed on a lower end of the outer sleeve in left and right directions, and the two turning covers each are provided with a semicircular sealing gasket.

9. The silty floating mud collection device as in claim 8, wherein end portions of the two turning covers are lap-jointed to each other through an inclined plane.

10. The silty floating mud collection device as in claim 9, wherein two sides of the control ring are in contact with the two turning covers, and an upper edge of one side of the two sides is higher than an upper edge of the other side of the two sides.

* * * * *